(12) United States Patent
Allibert et al.

(10) Patent No.: US 7,358,075 B2
(45) Date of Patent: Apr. 15, 2008

(54) ASSAY FOR PORCINE CIRCOVIRUS PRODUCTION

(75) Inventors: Patrice Allibert, Athens, GA (US);
Lionel Pierre Christian Cupillard, Bougoin Jallieu (FR); Jean Reyes, Lyons (FR)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 11/403,497

(22) Filed: Apr. 13, 2006

(65) Prior Publication Data

US 2006/0246425 A1    Nov. 2, 2006

Related U.S. Application Data

(60) Provisional application No. 60/670,892, filed on Apr. 13, 2005.

(51) Int. Cl.
*C12N 7/00* (2006.01)
(52) U.S. Cl. .................... 435/235.1; 435/325
(58) Field of Classification Search ............... 435/69.1, 435/325, 235.1
See application file for complete search history.

(56) References Cited

OTHER PUBLICATIONS

Liu et al. Virology, 2001, vol. 285, pp. 91-99.*
Gilpin et al. Veterinary Immunology and Immunopathology, 2003, vol. 94, pp. 149-161.*
Meerts et al. Archives of Virology, Mar. 2005, vol. 150, pp. 427-441.*
McNeilly, F., et al.: Production, Characterisation and Applications of Monoclonal Antibodies to Procine Circovirus 2, Archives of Virology, New York, NY, vol. 146, No. 5, 2001, p. 909-922.

\* cited by examiner

*Primary Examiner*—Ali R. Salimi
(74) *Attorney, Agent, or Firm*—Judy Javecki-Black; Thomas Kowalski, Esq.; Merial Limited

(57) ABSTRACT

The present invention provides methods for the determination of the viral titer of a culture of host animal host cells infected with a circovirus. The FACS-based methods of the invention may include determining the viability of the host cells in a cell culture medium supernatant and of those cells that remain adherent to a solid support. Detecting and measuring the percentage of cells that expressed the viral antigens ORF1 and ORF2 may determine the viral load of the cultured host cells. The yield of the virus may be established by the detection and measurement of both antigens in supernatant cells, for example 5 to 7 days from when the host cells are transferred to a serum free medium. The methods of the invention may yield rapid quantitative data. This allows the repeated in-process monitoring of the viral production throughout the incubation period, and ready selection of the most appropriate harvesting point.

3 Claims, 7 Drawing Sheets

ASSAY FOR PORCINE CIRCOVIRUS PRODUCTION

RELATED APPLICATIONS

This application claims priority to Provisional U.S. Application Ser. No. 60/670,892 filed Apr. 13, 2005, the contents of which are hereby expressly incorporated herein by reference.

INCORPORATION BY REFERENCE

All documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention

FIELD OF THE INVENTION

This invention relates to methods of in-process monitoring of a viral yield during batch incubation production processes using fluorescent antibody cell sorting analysis. This invention further relates to methods of in-process monitoring and harvesting of circovirus infected cell cultures in medium that may lack a serum component.

BACKGROUND OF THE INVENTION

Postweaning multisystemic wasting syndrome (PMWS) is a recently recognized disease of young pigs. The PMWS syndrome detected in Canada, the United States and France is clinically characterized by a gradual loss of weight and by manifestations such as tachypnea, dyspnea and jaundice. From the pathological point of view, it is manifested by lymphocytic or granulomatous infiltrations, lymphadenopathies and, more rarely, by hepatitis and lymphocytic or granulomatous nephritis (Clark E. G. (1997) Proc. Am. Assoc. Swine Prac. 499-501; La Semaine Veterinaire No. 26, supplement to La Semaine Veterinaire 1996 (834); La Semaine Veterinaire 1997 (857): 54; Nayar et al. (1997) Can. Vet. J. 38:385-387). Treatment and prevention of this disease are not currently available. Several lines of evidence, however, point to porcine circovirus as the etiologic agent of PMWS (Ellis et al. (1998) Can. Vet. J. 39:44-51). Circoviruses have been recovered from pigs with PMWS, and antibodies to porcine circovirus have been demonstrated in pigs with the disease.

A family of viruses, named Circoviridae, found in a range of plant and animal species and commonly referred to as circoviruses, are characterized as round, non-enveloped virions with mean diameters from 17 to 23.5 nm containing circular, single-stranded deoxyribonucleic acid (ssDNA). The ssDNA genome of the circoviruses represent the smallest viral DNA replicons known. As disclosed in WO 99/45956, at least six viruses have been identified as members of the family according to The Sixth Report of the International Committee for the Taxonomy of Viruses (Lukert et al. 1995, The Circoviridae, pp. 166-168. In Murphy, et al. (eds.) Virus Taxonomy, Sixth Report of the International Committee on Taxonomy of Viruses, Arch. Virol. 10 Suppl.).

Animal viruses included in the family are chicken anemia virus (CAV); beak and feather disease virus (BFDV); porcine circovirus (PCV); and pigeon circovirus. PCV was originally isolated from porcine kidney cell cultures. PCV replicates in the cell nucleus and produces large intranuclear inclusion bodies. See Murphy et al. (1999, Circoviridae p. 357-361, Veterinary Virology, 3rd ed. Academic Press, San Diego). There are currently two recognized types of PCV, PCV type 1 (PCV1) and PCV type 2 (PCV2). PCV1, isolated as a persistent contaminant of the continuous porcine kidney cell line PK-15 (ATCC CCL31), does not cause detectable cytopathic effects in cell culture and fails to produce clinical disease in pigs after experimental infection (see Allan G. (1995) Vet. Microbiol 44: 49-64; Tischer et al. (1982) Nature 295:64-66; and Tischer et al. (1986) Arch. Virol 91:271-276).

It is only very recently that some authors have thought that strains of PCV could be pathogenic and associated with the PMWS syndrome (Nayar et al. (1997) Can. Vet. J. 38: 385-387 and Clark E. G. (1997) Proc. Am. Assoc. Swine Prac. 499-501). Nayar et al. have detected PCV DNA in pigs having the PMWS syndrome using PCR techniques. PCV2, in contrast to PCV1, is closely associated with post weaning multisystemic wasting syndrome (PMWS) in weanling pigs (see Allan et al. (1998) Eur. J. Vet. Diagn. Investig. 10:3-10; Ellis et al. (1998) Can. Vet. J. 39:44-51 and Morozov et al. (1998), J. Clin. Microbiol. 36:2535-2541).

The nucleotide sequences for PCV1 are disclosed in Mankertz et al. (1997) J. Virol. 71:2562-2566) and Meehan et al. (1997) J. Gen. Virol. 78:221-227) and the nucleotide sequences for PCV2 are disclosed in Hamel et al. (1998) J. Virol. 72:5262-5267; Mankertz et al. (2000) Virus Res. 66:65-77 and Meehan et al. (1998) J. Gen. Virol. 79:2171-2179. Strains of PCV2 are disclosed in WO 00/01409 and have been deposited at the European Collection of Cell Cultures, Centre for Applied Microbiology & Research, Porton Down, Salisbury, Wiltshire SP4 OJG, United Kingdom and include: Accession No. V97100219; Accession No. V9700218; Accession No. V97100217; Accession No. V98011608; and Accession No. V98011609. WO 00/77216 also discloses PCV2.

As many as thirteen open reading frames (ORFs) have been identified in the PCV2 genome. ORF1 (Meehan et al., (1998)), alternatively designated as ORF4, comprises the nucleotides 398-1342 (GenBank Accession No. AF055392) and has the potential to encode a protein with a predicted molecular weight of 37.7 kD. ORF2 (Meehan et al., (1998); alternatively designated as ORF13, comprises the nucleotides 1381-1768 joined to 1-314 (GenBank Accession No. AF055392) and may encode a protein with a predicted molecular weight of 27.8 kD. Further description of the PCV2 ORFs 1-13 may be found in U.S. Pat. Nos. 6,368,601, 6,391,314, 6,660,272, 6,217,883, 6,517,843, 6,497,883 as well as AU 764379, EP 1019510, MX 221562, MX 216996, RU 2237492 and NZ 505008 which are incorporated herein by reference in the entirety.

ORF1 of PCV2 is highly similar (86% identity) to the ORF1 of the PCV1 isolate (Meehan et al., (1998)). The ORF1 protein of PCV1 has been partially characterized (Meehan et al., 1997; Mankertz et al., (1998) Virus genes 16:267-276) and has been shown to be essential for virus replication, most probably involved in the viral DNA replication.

Protein sequence identity between the respective ORF2s was lower (66% identity) than that between the ORF1s, but each of the ORF2s shared a highly conserved basic N-terminal region, similar to that observed in the N-terminal region of the major structural protein of the avian circovirus chicken anemia virus (CAV) (Meehan et al., 1998). Recently, Mankertz et al., in (1998) J. Gen. Virol. 79:381-384 has suggested that the ORF2 of the PCV1 isolate (designated ORF1 in Mankertz et al., 1998) codes for a capsid protein. The transcription analysis of the genome of PCV2 has not been published yet. Recent data obtained with the PCV1 isolate indicated that the ORF2 transcript is spliced (Mankertz et al., 1998).

Published studies to date on PCV2 used either tissue homogenate or cultured virus derived from field isolates. Tischer et al. ((1987) Arch Virol. 96:39-57) report that porcine kidney cells are stimulated to entry to the S phase in the cell cycle by D-glucosamine treatment. However, the treatment must be performed with caution because D-glucosamine is toxic for cell culture (see, Allan et al. (2000) J. Vet. Diagn. Investigation. 12:3-14).

There is a remaining need for methods for culturing circovirus including, for example, PCV1, PCV2 and other circoviruses, such that circovirus in high yield is possible. Such methods would be advantageous, in particular for preparation of PCV2 antigens as vaccines directed against PMWS. The present invention addresses that need. The invention relates to methods for growing and quantifying the infectious or antigenic amount and determining antibodies against circoviruses, in particular porcine circoviruses (PCV) that allow for in-process monitoring of the progress of the production of the virus in the batch culture.

Although porcine circovirus can be detected as a contaminating agent in pig tissue cultures, successful large-scale batch cultures of the virus require rapid assays to allow continual monitoring of the progress of viral production to obtain optimal yields. The object of the present invention, therefore, was to develop a method for monitoring the progress of the cultivation of a circovirus such as a porcine circovirus in vitro to be able to examine the ORFs kinetic expression. It was also intended to increase virus yield of a cell culture for the production of a vaccine that may require inactivated PCV or an avirulent PCV strain (e.g. through selection of an avirulent PCV strain after adaptation to various cell cultures and/or after treatment of infected cell cultures with mutagens or after genetic modification of the PCV) as live vaccine. In addition, the antigenic material obtained from grown porcine circoviruses can also be employed for diagnostic purposes. There is a need, therefore, to be able to periodically and rapidly monitor the progress of a batch cell culture of a circovirus under conditions that provide viral particles suitable for vaccine or other purposes. There is a need for monitoring methods that can give rapid results, rather than the labor-intensive and time-consuming methods currently employed for that purpose.

Citation or identification of any document in this application is not an admission that such document is available as prior art to the present invention.

SUMMARY OF THE INVENTION

This invention provides a FACS-based procedure for the in-process monitoring and rapid determination of the useful harvesting point of a cell culture infected with a circovirus such that an optimum yield of the virus can be obtained. The methods encompass providing a seed culture of circovirus infected host cells and inoculating a batch culture therewith, incubating the seed culture, removing aliquots of the cultured cells, separating supernatant cells and adherent cells, releasing the adherent cells from their substratum, determining the viability of the host cells, and determining the percentage of ORF1- and ORF2-positive cells by FACS, thereby determining the harvesting point of the culture.

One aspect of the invention provides a FACS-based method for detecting the production of circovirus antigen by a culture of host cells, wherein the method may encompass the steps of obtaining from a host cell culture infected with a circovirus a sample comprising a population of non-adherent host cells and a population of host cells adhering to a substratum, isolating from the sample the non-attached host cells thereof, isolating from the sample the adherent host cells and the substratum thereof and releasing the adherent host cells from the substratum, determining the amount of ORF1 in the non-adherent and released adherent host cells by contacting said cells with an ORF1-specific antibody, determining the percentage of infected cells in the non-adherent and released adherent host cells by contacting said cells with an ORF2-specific antibody, and relating the percentage of ORF1- and ORF2-positive cells in the sample to the amount of circovirus in the sample.

In various embodiments of the method, the circovirus can be PCV2. In various embodiments, the host cell strain can be PK-15 or other suitable cell lines. It is contemplated, however, that the methods of the invention can be usefully applied for detecting and in-process monitoring of the production of any circovirus cultured on isolated host cells and for which there are available viral antigen specific antibodies.

Another aspect of the invention provides a FACS-based method for in-process monitoring of the production of a circovirus from cultured host cells, encompassing the steps of obtaining from a host cell culture infected with a circovirus a time-dependent plurality of samples, each sample in the series comprising a population of non-adherent host cells and a population of host cells adhering to a substratum, isolating from each sample of cell culture the non-attached host cells thereof, isolating from each sample of cell culture the adherent host cells and the substratum thereof and releasing the adherent host cells from the substratum, determining the viability of the host cells in the samples by measuring propidium iodide uptake using flow cytometry, determining the percentage of ORF1-positive cells present in the non-adherent and released adherent cells determining the amount of ORF1 in the non-adherent and released adherent host cells by contacting said cells with an ORF1-specific antibody, determining the amount of the antibody binding to the cells by FACS and relating the amount of bound antibody to the amount of ORF1 present in the cells, determining the percentage of ORF2-positive cells present in the non-adherent and released adherent cells by determining the amount of ORF2 in the non-adherent and released adherent host cells by contacting said cells with an ORF2-specific antibody, determining the amount of the antibody binding to the cells by FACS and relating the amount of bound antibody to the amount of ORF2 present in the cells, and plotting the changes in the levels of viability, ORF1 and ORF2, thereby determining the time course of the production of the circovirus in the host cell culture.

In one embodiment of this method of the invention, the viability of the cells can be determined with propidium iodide and flow cytometry.

In the various embodiments of this method of the invention, the circovirus can be PCV2 and the host cell strain can be PK-15, although the methods should not be construed as to be applicable solely to this strain of circovirus/host cell combination.

Yet another aspect of the invention is a method of producing circovirus in yields that may be useful, for example, the preparation of a vaccine, encompassing the steps of preparing a seed culture of a circovirus by in-process monitoring of the expression of ORF1 and seeding a host cell culture with a seed culture of a circovirus, incubating the host cell culture in the absence of fetal calf serum, monitoring (i) viability of the host cells, and (ii) ORF1 and ORF2 expression by the host cells, and harvesting the circovirus from the host cell culture when ORF2 expression is approximately the same in the non-adherent cells and adherent cells of the host cell culture.

In various embodiments of this aspect of the invention, the yield of circovirus in the seed culture may be determined by monitoring the expression of circovirus ORF1 and ORF2 antigens in supernatant host cells using a fluorescent antibody cell sorting (FACS)-based method, and wherein the seed culture is harvested when ORF2 is expressed by the non-adherent cells.

In the various embodiments of this aspect of the invention, the viability of the cells may be determined by measuring propidium iodide uptake using flow cytometry.

In the various embodiments of this method of the invention, the circovirus can be PCV2 and the host cell strain can be PK-15, although the methods should not be construed as to be applicable solely to this strain of circovirus/host cell combination. It is contemplated, however, that the methods of the invention can be usefully applied for detecting and in-process monitoring of the production of any circovirus cultured on isolated host cells and for which there are available viral antigen specific antibodies.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

The following detailed description, given by way of examples, but not intended to limit the invention solely to the specific embodiments described, may best be understood in conjunction with the accompanying drawings, incorporated herein by reference, in which.

DETAILED DESCRIPTION

Figure 1:
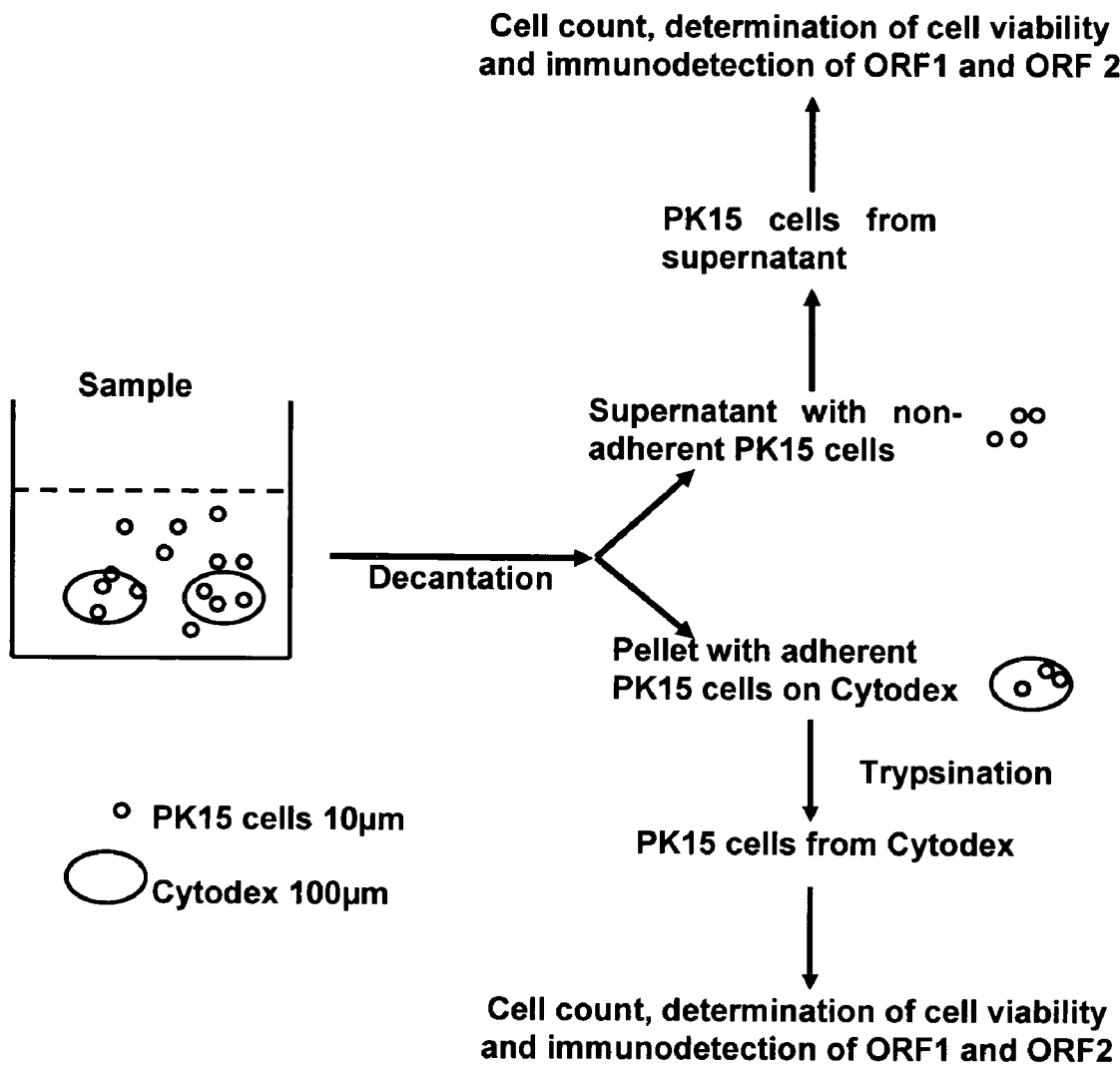
FIG. 1 illustrates a schema for the separation of supernatant and adherent PK-15 cells from a cell culture and determination of viral antigens ORF1 and ORF2 therein.

Various documents are cited in the following text, and various documents are referenced or cited in documents cited in the following text. There is no admission that any of these documents are indeed prior art as to the present invention. All documents cited herein and all documents referenced or cited in documents cited herein are hereby incorporated herein by reference.

The term "flow cytometer" as used herein refers to any device that will irradiate a particle suspended in a fluid medium with light at a first wavelength, and is capable of detecting a light at the same or a different wavelength, wherein the detected light indicates the presence of a cell or an indicator thereon. The "flow cytometer" may be coupled to a cell sorter that is capable of isolating the particle or cell from other particles or cells not emitting the second light. The indicator on the cell surface may be an antibody coupled to a fluorophore such as, but not limited to, FITC providing Flourescent Antibody Cell Sorting (FACS).

The term "host cell" as used herein refers to an isolated cell that is a host for the infection and replication of a virus, preferably a circovirus.

The terms "adherent cells" as used herein refers to animal cells grown in vitro and which have attached to a substratum. The substratum may be the surface of a culture container or, as in batch cell cultures, may be a particulate solid support such as CYTODEX™ (Amersham Biosciences, Inc) beads or the like. Such cells may be removed from the underlying solid support by methods requiring enzymatic digestion of the subcelluar matrix, including digestion under controlled conditions using a protease such as, but not limited to, trypsin. Conversely, term "non-adherent cells" refers to those cultured cells that have detached from a substratum during the course of the culture period.

As used herein, genes, gene loci or transcripts thereof have italicized designators; and protein or polypeptides expressed therefrom have non-italicized designators.

The terms "ORF1" and "ORF2" as used herein refer to circoviral antigens expressed from the open-reading frames ORF1 and ORF2 (as designated by Meehan et al., (1998) J. Gen. Virol. 78:221-227) respectively. ORF1 is believed to be an early-stage replicase and ORF2 a polypeptide contributing to the viral capsid. Thirteen open reading frames (ORFs) have been identified in the PCV2 genome. Further description of the PCV2 ORFs may be found in U.S. Pat. Nos. 6,368,601, 6,391,314, 6,660,272, 6,217,883, 6,517,843, 6,497,883 as well as AU 764379, EP 1019510, MX 221562, MX 216996, RU 2237492 and NZ 505008 which are incorporated herein by reference in the entirety. Correspondence between the various designations assigned to each ORF of PCV2 is shown in Example 1 below. As used herein, ORF1 and ORF2 correspond to ORF4 and ORF13 (as designated in the above-referenced patents) respectively.

The term "in-process" refers to the monitoring of parameters that are characteristic of cell and virus culture, including a virally infected cell culture, throughout the period of the culture. The monitoring can be continuous, such as monitoring the pH or oxygen content of the culture medium, or can be periodic monitoring wherein samples are withdrawn from the culture at selected time points, parameters such as viability or viral antigen content are detected and measured and the parameters are plotted versus the time of the culture.

The term "seed culture" as used herein refers to a culture of host cells infected with a selected virus such as a circovirus and which is then incubated for a period to allow the titer of virus to increase. Typically, but not necessarily, the volume of a seed culture is less than the volume of the subsequent main culture or fermentation medium that receives the seed culture.

Following longstanding law convention, the terms "a" and "an" as used herein, including the claims, are understood to mean "one" or "more".

Abbreviations: ORF, open reading frame; ORF, nucleotide sequence encoding an ORF; PK, porcine kidney; PCV, Porcine Circo Virus; PK-15, porcine kidney cells; FACS, fluorescent antibody cell sorting; ELISA, enzyme-linked immunosorbant assay; Mab, monoclonal antibody; FITC, Fluorescein isothiocyanate; IgG, immunoglobulin G; PBS/BSA, phosphate buffered saline/bovine serum albumen.

The present invention provides methods for the determination of the viral yield of a culture of host animal cells infected with a circovirus, in particular a porcine circovirus. The methods of the invention, however, are generally applicable to any other strain or type of circovirus growing on cell culture, especially in batch culture procedures. The methods of the invention are particularly useful for the monitoring of the viral yield of batch cultures of the porcine circovirus strain PCV2.

The FACS-based methods of the invention comprise determining the viability of the host cells in a cell culture medium supernatant and of those cells that remain adhered to a solid support such as, but not limited to, CYTODEX™ (Amersham Biosciences, Inc). The viral load of the cultured host cells is measured by determining the percentage of ORF1-positive cells present in the non-adherent and released adherent cells, determining the percentage of ORF2-positive cells present in the non-adherent and released adherent cells, relating the percentage of ORF1- and ORF2-positive cells in the sample to the amount of circovirus in the sample. The yield of the virus is established by detection and measurement of both antigens in supernatant cells, for example 5 to 7 days from when the host cells are transferred to a serum free medium.

One embodiment of the invention, therefore, is a novel assay suitable for the titration of PCV2 based on the immunodetection in PK-15 host cells of viral protein by flow cytometry using monoclonal antibodies specific for either ORF1 or ORF2. Furthermore, the kinetics of PK-15 cells growth can also be monitored by flow cytometry. The rapidity of the methods of the invention allows for the determination of an optimum harvesting point to achieve high viral yields. A harvesting point can be selected that offers a viral yield useful, for example, for the production of a vaccine, while minimizing the incubation period of the cells with attendant cost reductions. The methods of the invention rapidly yield quantitative data. This allows for the repeated monitoring of the viral production throughout the course of the incubation period and ready selection of the most appropriate harvesting point.

Traditional methods of measuring viral titer are much slower and involve extended culturing of test samples to form countable plaques. Conventional plate assays of the virus growing on PK-15 cells that are based on immunofluorescence detection using an ELISA based on an ORF2 monoclonal antibody are time consuming and labour intensive, requiring several days to obtain a useful result.

One aspect of the invention is a method for rapidly determining the viability characteristics of cultured host cells during the time course of a batch culture. Although the method is useful and suitable for monitoring the culture of any cells for viral production, the methods are particularly useful for the in-process control of cell cultures of PK-15 cells for the production of batches of PCV2 circovirus for vaccine production.

In this aspect of the methods according to the invention, and as illustrated in FIG. 1, samples of batch cell cultures are divided into a population of supernatant (non-adherent) cells and a population of cells adherent to a solid substratum. A substratum for use in culturing the host PK-15 cells, for example, is CYTODEX™ (Amersham Biosciences, Inc) beads, although any other suitable material known to those with skill in the art of tissue culture can be selected. Dense substratum beads are allowed to settle by gravity and the supernatant culture medium with the non-adherent cells is removed by any of a variety of methods such as aspiration, decantation, centrifugation and the like. The cells adherent to the substratum may then released from the substratum by, for example, trypsinization, the degree of the digestion release being monitored under a microscope to establish the point of maximum release of the cells from the substratum, with minimal damage to the cells themselves. The released cells are collected to yield the second of the two desired cell populations.

Described herein are methods for the production of the antibodies capable of specifically recognizing one or more epitopes of the ORF1 or ORF2 protein of a circovirus such as, but not limited to, PCV2. Such antibodies may include, but are not limited to polyclonal antibodies, monoclonal antibodies (mAbs), chimeric antibodies, single chain antibodies, Fab fragments, F(ab')$_2$ fragments, fragments produced by a FAb expression library, anti-idiotypic (anti-Id) antibodies, and epitope-binding fragments of any of the above. Advantageously, the antibodies for use in the present invention are monoclonal antibodies specific for either the ORF1 or the ORF2 protein expressed by the ORF1 and ORF2 genes of a circovirus. Most advantageously, the ORF1 or ORF2 proteins are expressed by the circovirus PCV2.

For the production of antibodies, various host animals may be immunized by injection with an isolated ORF1 or ORF2 polypeptide or an immunogenic peptide thereof. Such host animals may include but are not limited to rabbits, mice, and rats, to name but a few. Various adjuvants may be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Following completion of the immunization steps, antisera reactive with the ORF1 or ORF2 protein may be collected and, if desired, polyclonal anti-ORF1 (or anti-ORF2) protein antibodies isolated.

Polyclonal antibodies are heterogeneous populations of antibody molecules derived from the sera of animals immunized with an antigen, such as a target gene product, or an antigenic functional derivative thereof. For the production of polyclonal antibodies, host animals such as those described above, may be immunized by injection with the ORF1 or ORF2 protein supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler & Milstein (1975) Nature 256: 495-497; and U.S. Pat. No. 4,376,110), the human B-cell hybridoma technique (Kosbor et al. (1983) Immunology Today 4: 72; Cole et al. (1983) Proc. Natl. Acad. Sci. U.S.A. 80: 2026-2030), and the EBV-hybridoma technique (Cole et al. (1985) Monoclonal Antibodies And Cancer Therapy Alan R. Liss, Inc. pp. 77-96). Briefly, spleen cells are harvested from an immunized mouse and fused with immortalizing cells (i.e., myeloma cells) to yield antibody-producing hybridomas. Hybridomas can be screened immunochemically for production of monoclonal antibodies specifically reactive with the ORF1 or ORF2 protein. Commercial sources for obtaining custom polyclonal antisera and monoclonal antibodies are also available. For example, HTI Bio-Products, Inc. (Ramona, Calif.) produces custom-made antibodies, antisera, ascites fluid and hybridoma lines.

Protocols for producing, isolating and purifying conventional and monoclonal antibodies may be analogous to those described in Cassone et al. (1988) J. Med. Microbiol. 27: 233-238; Hancock & Evan Production and Characterization of Antibodies against Synthetic Peptides pp 23-33 in Immunochemical Protocols ed. M. M. Manson, (1992) (Humana Press, Totowa, N.J.); Goding, J. W., Monoclonal Antibodies: Principles and Practice, 2d ed., (1986) (Academic Press Ltd., London) and Lam & Mutharia, "Antigen-Antibody Reactions," pp 104-132 in Methods for General and Molecular Bacteriology, ed. P. Gerhardt, (1994) (ASM Press, Washington, D.C.) the contents of which are incorporated herein by reference in their entirety. Such antibodies may be of any immunoglobulin class including IgG, IgM, IgE, IgA, IgD and any subclass thereof. The hybridoma producing the MAbs of this invention may be cultivated in vitro or in vivo. Production of high titers of MAbs in vivo makes this the presently preferred method of production.

Alternatively, techniques described for the production of single chain antibodies such as, but not only U.S. Pat. No. 4,946,778; Bird (1988) Science 242: 423-426; Huston et al. (1988) Proc. Natl. Acad. Sci. 85: 5879-5883; and Ward et al. (1989) Nature 334: 544-546 can be adapted to produce the ORF1 or ORF2 protein-specific antibodies. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al. (1989) Science 246: 1275-1281) to allow rapid and easy identification of monoclonal Fab fragments with the desired specificity.

An antibody made according to the present invention can be used to detect the ORF1 (or ORF2) protein in or on cells, cell extracts, or in other biological preparations which can contain the ORF1 or ORF2 protein. Additionally, such an antibody can be labeled with a detector molecule to allow for detection of an antigen/antibody complex. Suitable labels include various enzymes, fluorescent molecules, radioactive labels, chemiluminescent molecules and the like. For example, enzymes useful for labeling antibodies include horseradish peroxidase and alkaline phosphatase. Fluorescent labels include, but are not limited to, fluorescein, rhodamine, dansyl chloride or phycoerythrin.

The viability of the two cell populations is determined, as described in Example 2 below, by mixing aliquots of the isolated cell populations with propidium iodide that is taken up into the cell nuclei only by non-viable cells. The stained cells are analyzed by flow cytometry to obtain total cell counts, as shown for example, in FIG. 2, as well as the proportions of live and dead cells in the sample population, as shown in FIG. 3.

In addition to the host cell viability measurements, the methods of the invention further comprise the steps of contacting the isolated cell populations with antibodies specific for the viral antigens ORF1 and ORF2, also as described in Example 2 below. The cells are subsequently washed and may be contacted with anti-IgG antiserum labeled with a flourophore such as, but not limited to, FITC before measuring the cell bound florescence by a flow cytometer, also as described in Example 2.

Figure 2:
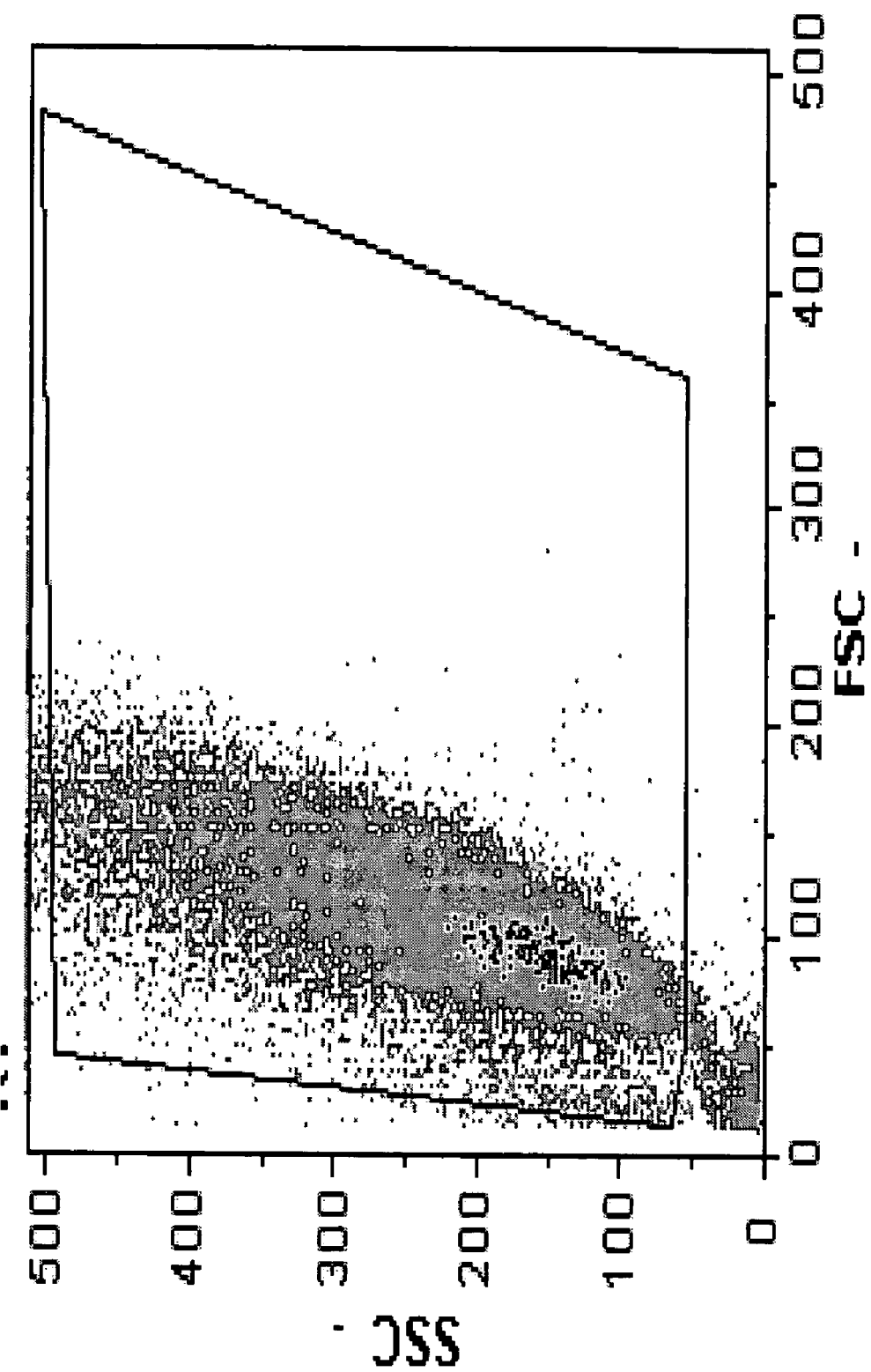
FIG. 2 illustrates the flow cytometry counting of total PK-15 cells in a cell suspension, including live and dead cells.
Figure 3:
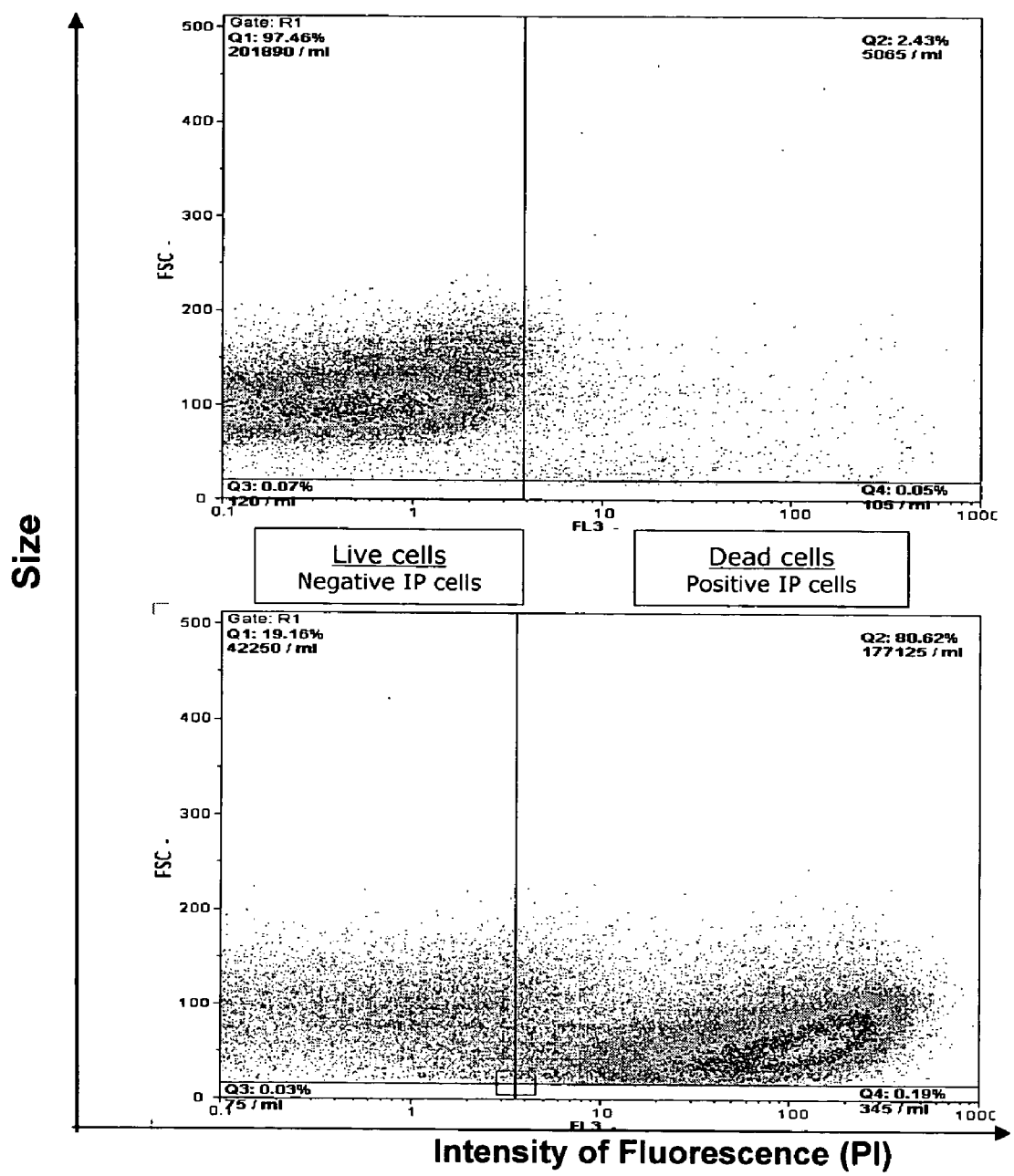
FIG. 3 illustrates the detection of the proportion of dead cells in a population of PCV2 infected PK-15 cells by the shift in propidium iodine uptake and FACS.
Figure 4:
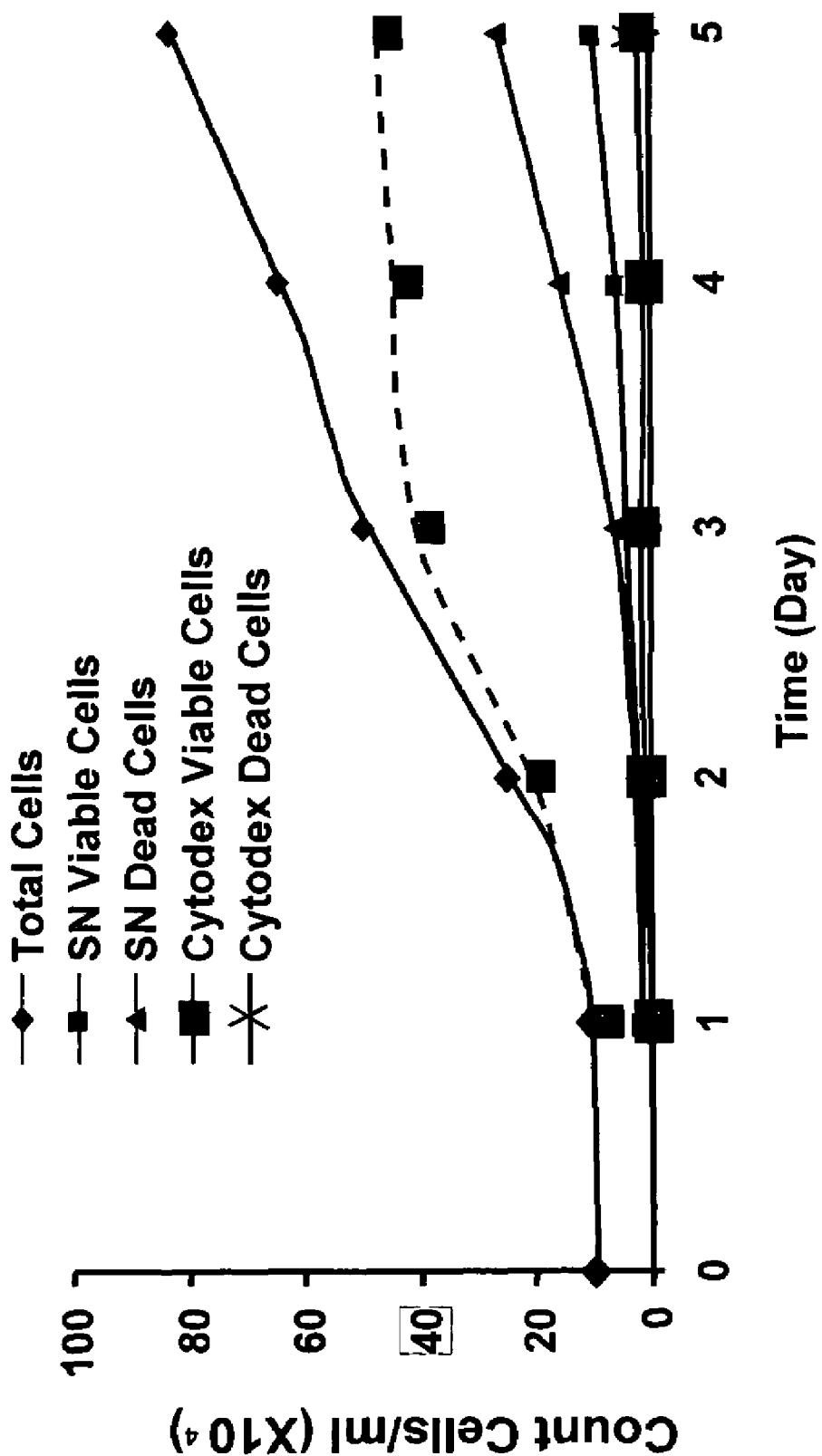
FIG. 4 illustrates a time course of viability of a working seed culture of PCV2 infected PK-15 cells with fetal calf serum present throughout the incubation period.
Figure 5:
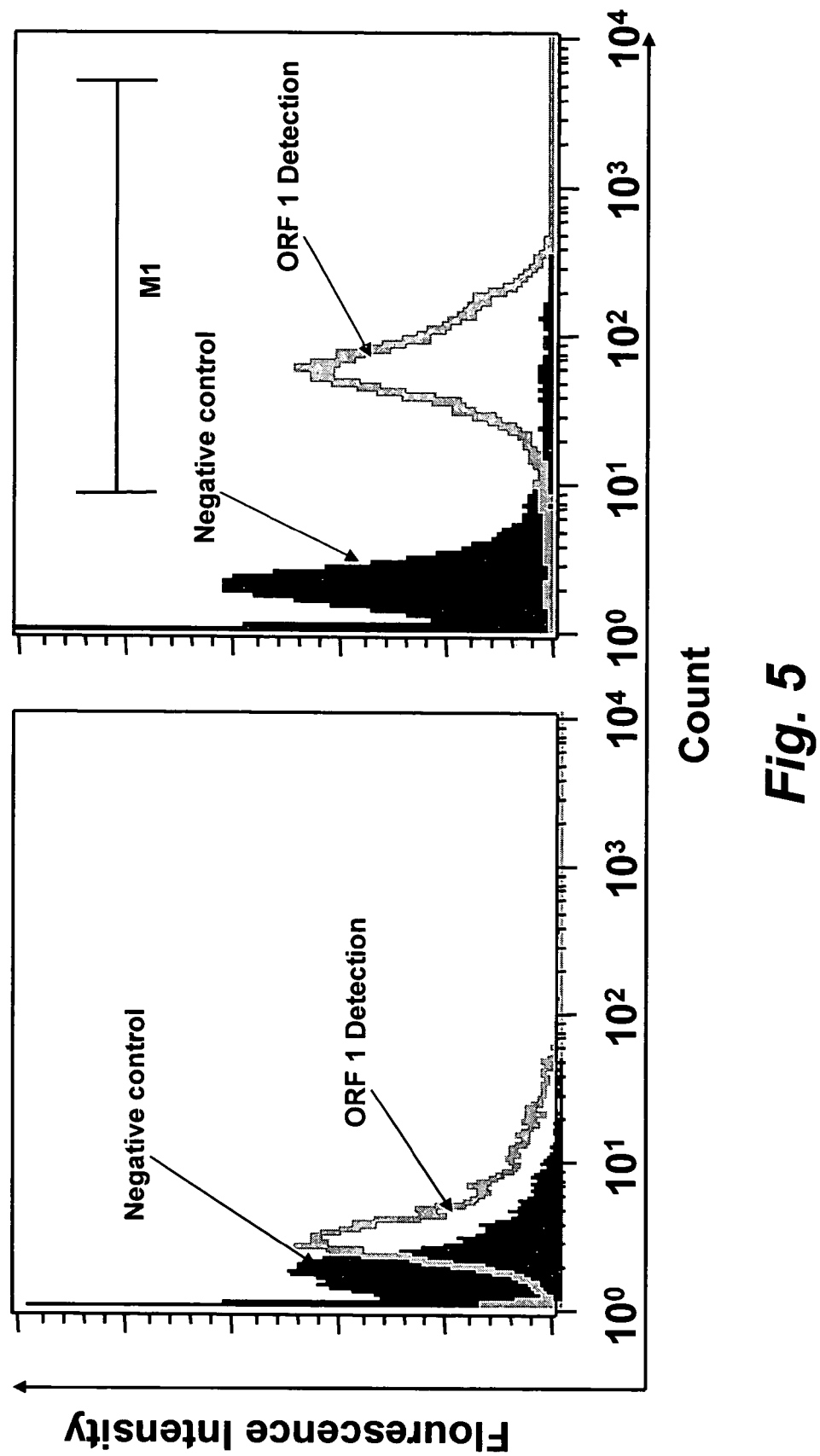
FIG. 5 illustrates ORF1 immunodetection and measurement by FACS.

Exemplary viability results for the growth of PCV2 virus on PK-15 cells grown in a liter batch culture with fetal calf serum in the medium are shown in FIGS. 2, 3 and 4. For example, in one experiment after five days incubation, about 50% of the total cultured cell population were located in the medium supernatant and were predominantly dead. This contrasted with the remaining 50% of the cells which were adherent to the CYTODEX™ (Amersham Biosciences, Inc) substratum and which were viable.

Figure 6:
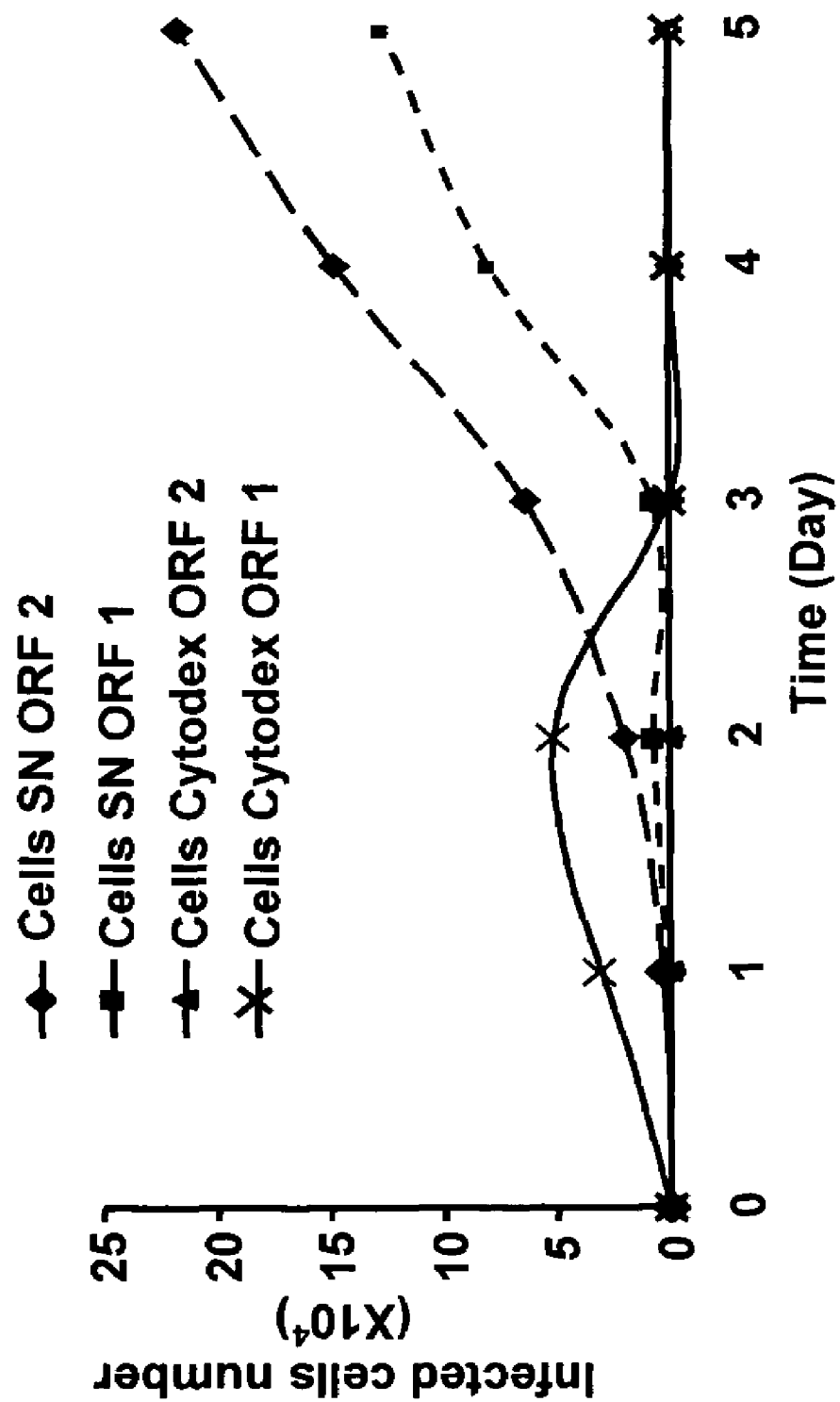
FIG. 6 illustrates the production of the PCV2 viral ORF1 and ORF2 antigens during the incubation period of a working seed culture.

Measurement of the viral production in the batch cultures containing fetal calf serum showed that ORF1 was transitorily expressed during days 1 and 2, and only in the substratum adhered cells. ORF1 was detected in the supernatant (or non-adherent) cells only from days 3 to 5 as shown, for example, in FIG. 6. The viral capsid antigen ORF2 was detectable only in the supernatant, non-adherent, cells with a continuous increase over the incubation period after the first day of incubation such as shown in FIG. 6.

The method of the invention allows the detection and monitoring of a circovirus and infected cells by detecting ORF1 and ORF2 expressed in supernatant (and therefore predominantly dead) cells until the harvest point. The rapidity with which these data are obtained permits frequent periodic monitoring of the progress of the infection of the cell culture. The culture may then be harvested at a point that gives a high yield of virus suitable for seeding a large batch host cell culture for the ultimate production of virus of sufficient quality and quantity for use in, for example, vaccine development and production.

The seed cultures developed as a result of the use of the methods of the invention can be used to seed large volume cell cultures, in the order of 100-1000 liter volumes. In this procedure, the seed culture harvested at day 5 or other time point as particularly indicated by ORF2 expression as determined above, is inoculated into a large-scale cell culture comprising cell culture medium containing fetal calf serum. The viability of the host cells, such as PK-15 cells, is then monitored according to the methods described in Example 2 below. After an initial incubation period which may be, but is not limited to, about 3 days, the cell culture medium can be exchanged with medium that does not include fetal calf serum, and the incubation is continued, again with periodic in-process sampling and determination as shown, for example, in FIG. 7.

Figure 7:
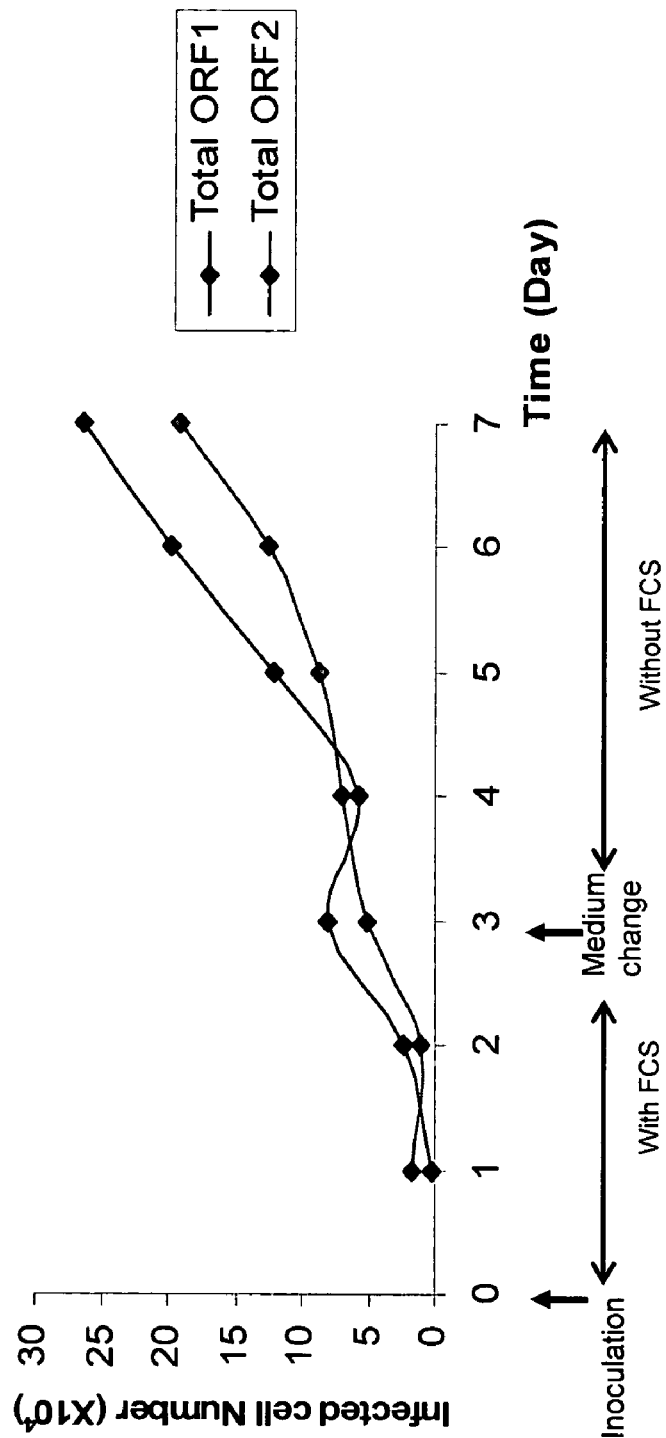
FIG. 7 illustrates the production of the viral antigens ORF1 and ORF2 in PK-15 cells infected with PCV2 virus with removal of FCS from the culture medium after 3 days.

Another aspect, therefore, of the invention is the in-process monitoring of the production of circovirus in large scale host cell cultures by monitoring the production of ORF1 and ORF2 using FACS. Using the methods of the invention as described in Example 2, the cell cultures may be monitored rapidly and more frequently when compared to conventional culture-based procedures so that the culture may be harvested once a desired viral yield has been attained. The cultures can be monitored for the expression of the viral-specific antigens ORF1 and ORF2 as shown, for example, in FIG. 7. Typically, the production of total ORF1 and ORF2 antigen, as shown in FIG. 7, mimics the pattern of host cell growth as illustrated in FIG. 7. For example, as described in Example 5 below, the markers ORF1 and ORF2 of PCV2 grown on PK-15 cells increase linearly from day 4 to day 7 and display similar patterns of increase for both adherent cells attached to a substratum and to the non-adherent cells in the medium supernatant.

Removal of the serum from the culture medium reduces and delays the onset of the viral antigen expression, particularly noticeable if the culture is harvested at day 5. Continuation of the culture beyond day 5 (as determined from the point of the seeding of the culture) can, however, significantly increase the yield of ORF2 antigen, that is, of mature viral particles (see FIG. 7).

This invention, therefore, provides a FACS procedure for the in-process monitoring and rapid determination of the useful harvesting point of a cell culture infected with a circovirus such that an optimum yield of the virus can be obtained. The methods comprise providing a seed culture of circovirus infected host cells and inoculating a batch culture therewith, incubating the seed culture, removing aliquots of the cultured cells, separating supernatant cells and adherent cells, releasing the adherent cells from their substratum, determining the viability of the host cells, determining the percentage of ORF1 and ORF2 in the cell sample by FACS, and determining the harvesting point of the culture.

One aspect of the invention provides a fluorescent antibody cell sorting (FACS)-based method for detecting the production of circovirus antigen by a culture of viral infected host cells, wherein the production of circovirus antigen is related to the percentage of open reading frame 1 (ORF1) and open reading frame 2 (ORF2) positive cells, comprising isolating (i) non-adherent host cells and (ii) adherent host cells released from the substratum from a sample comprising a population of non-adherent host cells and a population of host cells adhering to a substratum from a host cell culture infected with a circovirus, and determining (i) the percentage of open reading frame 1 (ORF1)-positive cells and (ii) the percentage of open reading frame 2 (ORF2)-positive cells present in the isolated non-adherent host cells and the adherent host cells released from the substratum.

In various embodiments of this aspect of the method, the circovirus can be PCV2. In various embodiments, the host cell strain can be PK-15. It is contemplated, however, that the methods of the invention can be usefully applied for detecting and in-process monitoring of the production of any circovirus cultured on isolated mammalian host cells and for which there are available viral antigen specific antibodies.

Another aspect of the invention provides a fluorescent antibody cell sorting (FACS)-based method for in-process monitoring of the production of a circovirus from cultured host cells, wherein plotting changes in levels of viability, ORF1 and ORF2, determines a time course of circovirus production in a host cell culture comprising isolating (i) non-adherent host cells and (ii) adherent host cells released from the substratum from a sample comprising a population of non-adherent host cells and a population of host cells adhering to a substratum from a host cell culture infected with a circovirus, determining viability of the non-adherent host cells and adherent host cells, and determining (i) the percentage of open reading frame 1 (ORF1)-positive cells and (ii) the percentage of open reading frame 2 (ORF2)-positive cells present in the isolated non-adherent host cells and the adherent host cells released from the substratum.

In one embodiment of this method of the invention, the viability of the cells is determined by measuring propidium iodide uptake using flow cytometry.

In the various embodiments of this method of the invention, the circovirus can be PCV2 and the host cell strain can be PK-15, although the methods should not be construed as to be applicable solely to this strain of circovirus/host cell combination. For example, the methods of the invention may be generally applicable to chicken anemia virus or beak and feather disease virus and host cells such as a suitable avian host cell and the like.

Yet another aspect of the invention is a method of producing circovirus in serum-free conditions and, therefore, useful for the preparation of a vaccine, comprising the steps of preparing a seed culture of a circovirus by in-process monitoring of the expression of ORF1 and seeding a host cell culture with a seed culture of a circovirus, incubating the host cell culture in the absence of fetal calf serum, monitoring (i) viability of the host cells, and (ii) ORF1 and ORF2 expression by the host cells, and harvesting the circovirus from the host cell culture when ORF2 expression is approximately the same in the non-adherent cells and adherent cells of the host cell culture.

In various embodiments of this aspect of the invention, the yield of circovirus in the seed culture may be determined by monitoring the expression of circovirus ORF1 and ORF2 antigens in supernatant host cells using a fluorescent antibody cell sorting (FACS)-based method, and wherein the seed culture is harvested when ORF2 is expressed by the non-adherent cells.

In the various embodiments of this aspect of the invention, the viability of the cells may be determined by measuring propidium iodide uptake using flow cytometry.

In the various embodiments of this method of the invention, the expression of ORF1 and ORF2 antigens in a viral infected host cell culture can be monitored using a fluorescent antibody cell sorting (FACS)-based method, wherein the production of circovirus antigen is related to the percentage of open reading frame 1 (ORF1) and open reading frame 2 (ORF2) positive cellsFACS.

In the various embodiments of this method of the invention, the circovirus can be PCV2 and the host cell strain can be PK-15, although the methods should not be construed as to be applicable solely to this strain of circovirus/host cell combination. It is contemplated, however, that the methods of the invention can be usefully applied for detecting and in-process monitoring of the production of any circovirus cultured on isolated mammalian host cells and for which there are available viral antigen specific antibodies.

It should be understood that the present invention is not limited to the specific compositions, equipment or methods described herein and that any composition having a formula or method steps equivalent to those described falls within the scope of the present invention. The method steps for determining the percentage of infected cells in a cell culture are merely exemplary so as to enable one of ordinary skill in the art to make the composition and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

The invention is further described by the following non-limiting examples:

EXAMPLES

Example 1

Correspondence Between the Designations of ORFs of Circovirus PCV2

The ORFs of circovirus PCV2, their equivalent designators, and the respective sources thereof, incorporated herein by reference in the entirety, are shown in Table 1 below. ORF1 and ORF2, as described by Meehan et al. (1997; 1998) have been alternatively designated as ORFs 4 and 13 respectively.

TABLE 1

PCV2 ORF numbering and equivalents

| ORF Numbering | Alternative Designations | |
|---|---|---|
| | Source | |
| Meehan et al. J. Gen. Virol. 78:221-227 (1997) | U.S. patent application Ser. No. 20020106639 to Wang et al. | U.S. patent Ser. Nos. 6,368,601, 6,391,314, 6,660,272, 6,217,883, 6,517,843, 6,497,883 |
| 1 | 1 | 4 |
| 2 | 6 | 13 |
| 3 | 2 | 7 |
| 4 | 3 | 10 |
| 5 | 4 | 5 |
| 6 | 5 | 3 |
| 7 | | 1 |
| 8 | | 2 |
| 9 | | 6 |
| 10 | | 8 |
| 11 | | 9 |
| 12 | | 11 |
| 13 | | 12 |

Example 2

Assay of Viability, Detecting ORF1 and ORF2 in PCV2-Infected PK-15 Cells (a) Determination of Cell Counts and Cell Viability Propidium iodide was used to assess plasma membrane integrity. Propidium iodide is a fluorescent vital dye that contains nucleic acid. Dead cells incorporate propidium iodide which was detected as a red stain by flow cytometry using a Galaxy cytometer (other similarly functioning models of flow cytometer may be used). This cytometer has the capability to differentiate, detect and count cells that are unstained (viable) or propidium iodide stained (dead). The number of cells in a volume of 200 µl is determined according to the manufacturer's instructions for the particular model of cytometer used.

1 ml of cell suspension was prepared in PBS in a tube specific for the Galaxy cytometer. The dilution of the cell suspension was adjusted to have between about $2 \times 10^4$ to about $1 \times 10^6$ cells per ml (corresponding to the linearity value of the cytometer count). To the cell suspension was added 5 µl of propidium iodide (50 µg/ml). The suspension was then vortex mixed for several seconds and analyzed immediately on the cytometer. Typical settings for the cytometer were: Threshold on FSC-lineage scale; Fluorescence of cells detected on FL3 log scale corresponding to the propidium iodide channel). The cytometer software gave the results of the counts automatically as dot plots such as shown in FIGS. 2 and 3.

(b) Determination of Percentage of Infected Cells by ORF1 and/or ORF2 Measurement Approximately $3 \times 10^6$ cells were required for a single assay, aliquoted as $1 \times 10^6$ for a negative control, $1 \times 10^6$ for the ORF1 detection and $1 \times 10^6$ for the ORF2 detection. For a different quantity of cells, the reagent volumes were adapted accordingly.

(i) Fixation: BD CytofixCytoperm (BD Biosciences, ref. 554714) was used. Fixation was performed according to the recommendations of the fixative manufacturer. Briefly, $3 \times 10^6$ cells were centrifuged for 6 mins at 400 g in a 15 ml or 50 ml conical tube. The supernatant was discarded, the cells were resuspended with 750 µl of Cytofix and incubated for 20 mins. on ice. The cells were washed twice with 1 ml of PBS containing 1% BSA and resuspended in 1 ml of PBS/1% BSA. Samples were stored at 5° Celsius for up to 15 days before staining (ii) Staining for ORF1 and ORF2: The fixed cells were centrifuged for 6 mins at 400 g, the supernatant discarded and 300 µl of 1× BD Perm/Wash solution was added. 100 µl of fixed cells was dispensed into 3 wells of 96 microwell plates and centrifuged for 6 mins. at 400 g. The supernatant was discarded and 100 µl of 1× BD Perm/Wash solution was added. 5 µl of an antibody (1 mg/ml) was added to each well. Typically, 5 µg of monoclonal antibody-purified Mab anti-PCV2 (ORF1) No 1991D3GA, Initial Concentration=1 mg/ml or purified Mab anti-PCV2 (ORF2) No 1903A8BC, Initial Concentration=1 mg/ml was sufficient for each stain. Purified Mab anti-clostridium N° 101B9B or equivalent, Initial Concentration=1 mg/ml, was used as a negative control.

The wells were incubated for 30 mins. on ice. The cells were washed twice with 1× BD Perm Wash solution (200 µl/wash/well). Then was added 100 µl of 1× BD Perm Wash solution containing 1 µl of anti mouse FITC (anti-mouse IgG conjugated with FITC (for example, Beckman, ref no. 115-095-146) or the equivalent thereof) per well and the wells incubated again for 30 mins. on ice. The cells were washed twice with 1× BD Perm Wash solution (200 µl/wash/well) and resuspended in 200 µl of PBS/1% BSA per well.

(iii) Detection by FCM: Settings parameters for the cytometer, such as a Galaxy Cytometer (Partec), were typically: Threshold on FSC-lineage scale; Fluorescence of cells detected on FL1 log scale (corresponding to the FITC channel).

Representative histograms showing in the fluorescence activity due to detection of ORF1 in a population of infected PK-15 host cells, compared to a negative control population of cells, is shown in FIG. 3. To calculate the percentage of infected cells, the percentage of negative cells was subtracted from the percentage of ORF cells. In the left-hand histogram, there were 0% infected cells, whereas in the right-hand example of FIG. 3, 88% of the cells were infected.

A typical distribution of live and dead cells as determined by granulometry is shown in FIG. 2 and a shift in the signal of propidium iodide fluorescence due to the death of an infected host cell population is shown in FIG. 4. In this case, 80% of the host cells were dead.

Example 3

PK-15 Count and Viability After PCV2 Inoculation in Batch Seed Cultures

As shown in FIG. 3, At day 5 of the incubation period of a batch seed culture of PCV2 virus growing on PK-15 cells, 50% of the host cells were located in the supernatant and were mostly dead (73%). In contrast, 50% of the host cells were located on the CYTODEX™ (Amersham Biosciences, Inc) substratum support and were almost entirely a viable population (96%).

PCV2-infected PK-15 cells were detected at the end of the culture at day 5, but only in the supernatant cells using flow cytometry to detect ORF1 and ORF2. As shown, for example, in FIG. 6, the kinetics of the viral-specific antigen formation was dependent on the ORF: ORF1 was produced early and at low levels whilst ORF was produced later in the incubation cycle and at increasing levels.

Example 4

ORF1 and ORF2 Total Staining

As shown in FIG. 6, for ORF1 there was no signal on cells membrane detected during the later phase of the culture incubation period. Table 2, below, shows that no membrane signals were detected on cells adherent to CYTODEX™ (Amersham Biosciences, Inc). Major ORF-specific signals were on cells from the culture supernatant and were increasing from day 2 to day 5. Results were similar for live or dead cells, with a maximum of 60% at day 4.

TABLE 2

|  | Cells from supernatant |  | Adherent cells |  |
|---|---|---|---|---|
| Count (total/ml) | $3.6 \times 10^5$ |  | $4.7 \times 10^5$ |  |
| % of Total Cells | 43% |  | 57% |  |
| Staining | Membrane | Membrane + Intracellular compartments. | Membrane | Membrane + Intracellular compartments. |
| ORF1 | <3% | 35% | <3% | <3% |
| ORF2 | 37% | 60% | <LOQ | <LOQ |

Example 5

Culturing of PCV2 Circovirus on PK-15 Cells in Large Scale Batch Culture with Serum Removal after 3 Days A 300-liter fermenter was seeded with a culture of PK-15 cells previously incubated for 5 days with PCV2 virus, in accordance with documents cited herein. After 3 days of culturing, the medium was exchanged for a growth medium lacking fetal calf serum. Samples taken at each day were tested for PK-15 viability and the expression of ORF1 and ORF2 as described in previous examples.

The time courses of the expression of the viral antigens ORF1 and ORF2 is illustrated in FIG. 7.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A method for the production of circovirus, comprising:
    seeding a host cell culture with a seed culture of a circovirus;
    incubating the host cell culture in the absence of fetal calf serum;
    monitoring (i) viability of the host cells using flow cytometry, and (ii) ORF1 and ORF2 expression by adherent and non-adherent host cells using a fluorescent antibody cell sorting (FACS)-based method; and
    harvesting the circovirus from the host cell culture when ORF2 expression is approximately the same in the non-adherent cells and adherent cells of the host cell culture.

2. The method according to claim 1, wherein the circovirus is PCV2.

3. The method according to claim 1, wherein the host cell is PK-15.

* * * * *